US012094350B2

(12) United States Patent
Nishimura et al.

(10) Patent No.: US 12,094,350 B2
(45) Date of Patent: Sep. 17, 2024

(54) CONTROL DEVICE, UNMANNED AERIAL VEHICLE, AND METHOD

(71) Applicant: TOYOTA JIDOSHA KABUSHIKI KAISHA, Toyota (JP)

(72) Inventors: Kazuya Nishimura, Anjo (JP); Shin Sakurada, Toyota (JP); Soutaro Kaneko, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 282 days.

(21) Appl. No.: 17/714,365

(22) Filed: Apr. 6, 2022

(65) Prior Publication Data

US 2022/0335838 A1    Oct. 20, 2022

(30) Foreign Application Priority Data

Apr. 16, 2021   (JP) ................................ 2021-069882

(51) Int. Cl.
| | | |
|---|---|---|
| G08G 5/00 | (2006.01) | |
| B64C 39/02 | (2023.01) | |
| B64U 101/60 | (2023.01) | |
| G01N 33/00 | (2006.01) | |

(52) U.S. Cl.
CPC ........... *G08G 5/006* (2013.01); *B64C 39/024* (2013.01); *G01N 33/0001* (2013.01); *G01N 33/0027* (2013.01); *G08G 5/003* (2013.01); *G08G 5/0069* (2013.01); *G08G 5/0091* (2013.01); *B64U 2101/60* (2023.01); *B64U 2201/10* (2023.01)

(58) Field of Classification Search
CPC .... G08G 5/006; G08G 5/0013; G08G 5/0039; G08G 5/0086; G08G 5/045; G01N 33/0001; G01N 33/0027; G05D 1/102; G06F 18/00; G06Q 10/30; G06Q 50/40; G06V 20/176; G06V 20/52
See application file for complete search history.

(56) References Cited

U.S. PATENT DOCUMENTS

| | | | | |
|---|---|---|---|---|
| 10,095,231 B2 * | 10/2018 | Gordon | .................. | G06V 20/17 |
| 2018/0074496 A1 | 3/2018 | Gordon et al. | | |
| 2018/0322794 A1 | 11/2018 | Beaurepaire et al. | | |

FOREIGN PATENT DOCUMENTS

| | | |
|---|---|---|
| CN | 106094869 A | 11/2016 |
| IN | 201911026357 A * | 1/2021 |
| JP | 2018-203056 A | 12/2018 |

OTHER PUBLICATIONS

"How Can Odors Be Measured? An Overview of Methods and Their Applications" C. Bax, S. Sironi, and L. Capelli. Atmosphere 2020, 11, 92; www.mdpi.com/journal/atmosphere (Year: 2020).*

* cited by examiner

*Primary Examiner* — Peter D Nolan
*Assistant Examiner* — Tanya C Sienko
(74) *Attorney, Agent, or Firm* — Oliff PLC

(57) ABSTRACT

The control device includes a control unit that is configured to control an unmanned aerial vehicle that collects a collection object. The control unit acquires information that indicates an odor intensity of the collection object to be collected, and determines a flight route of the unmanned aerial vehicle after the unmanned aerial vehicle picks up the collection object located at a collection point, based on the information that indicates the odor intensity of the collection object.

17 Claims, 5 Drawing Sheets

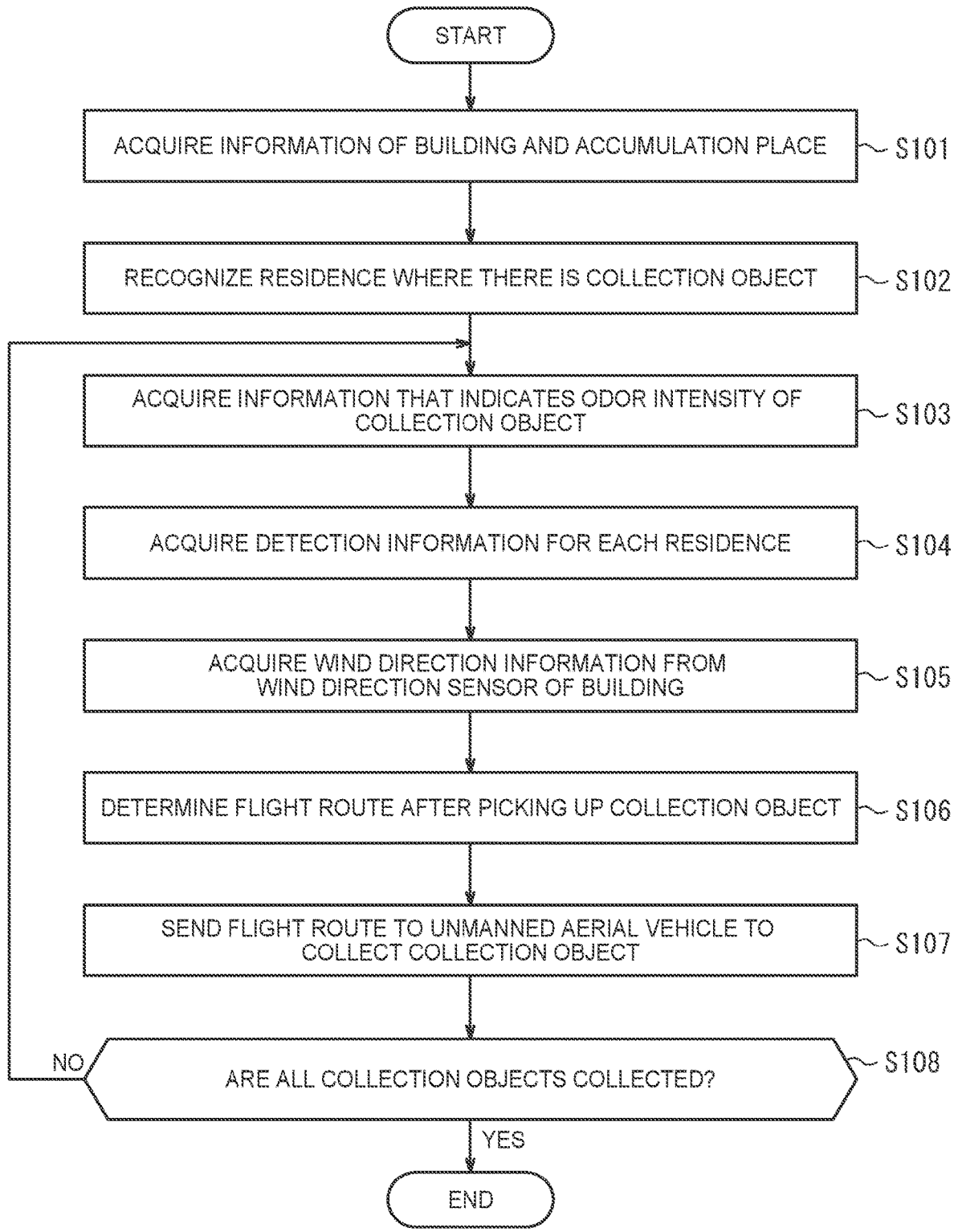

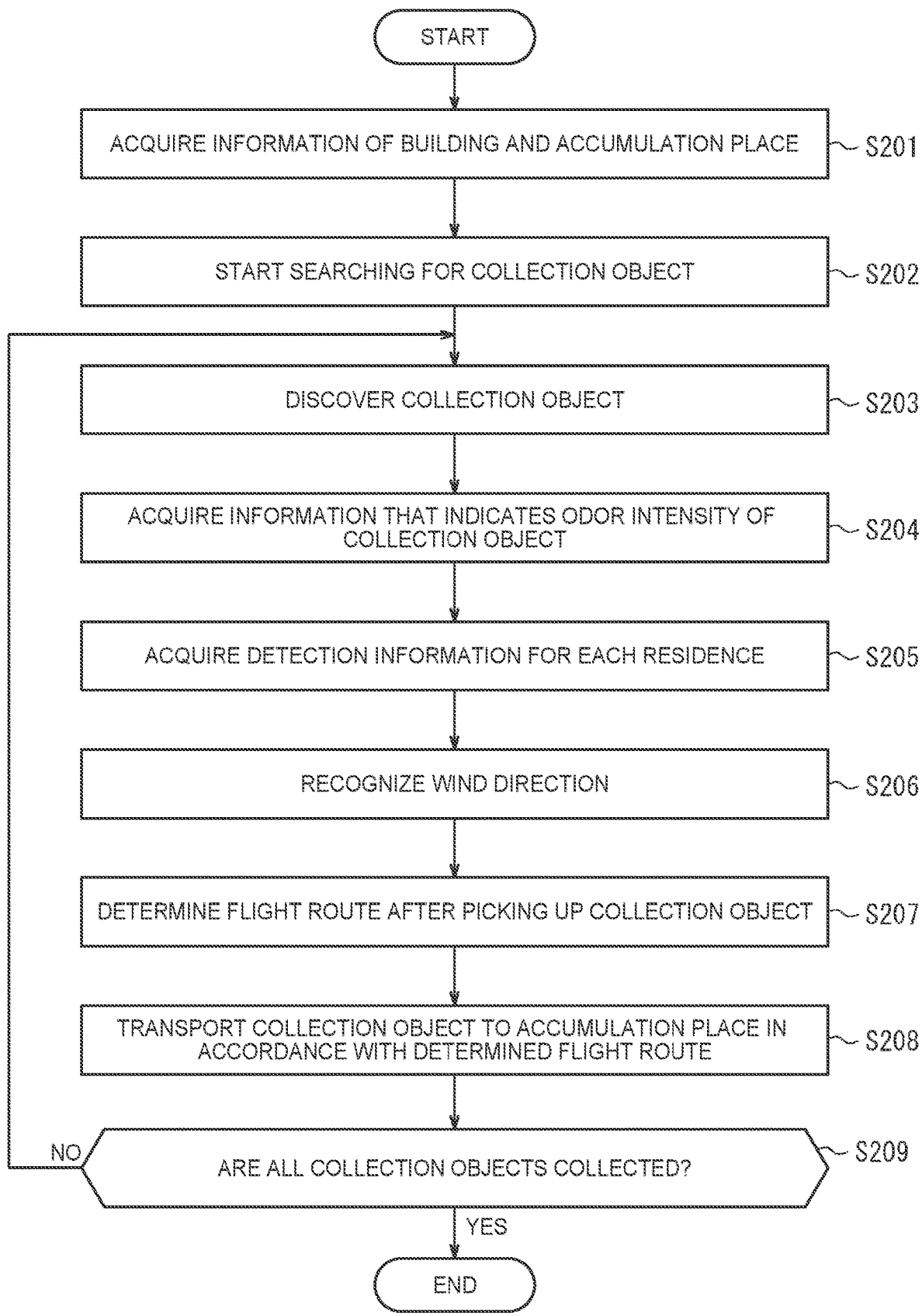

CONTROL DEVICE, UNMANNED AERIAL VEHICLE, AND METHOD

CROSS-REFERENCE TO RELATED APPLICATION

This application claims priority to Japanese Patent Application No. 2021-069882 filed on Apr. 16, 2021, incorporated herein by reference in its entirety.

BACKGROUND

1. Technical Field

The present disclosure relates to a control device, an unmanned aerial vehicle, and a method.

2. Description of Related Art

In recent years, a system has been proposed in which an article is delivered to a target place or collected from the target place using an unmanned aerial vehicle such as a drone. For example, Japanese Unexamined Patent Application Publication No. 2018-203056 (JP 2018-203056 A) describes that a storage device is installed on a balcony or the like of a building such as an apartment residence, and a drone enters the balcony and collects a load stored in the storage device.

SUMMARY

As one aspect of transporting an article by using an unmanned aerial vehicle, it is conceivable to transport a collection object such as garbage placed on a balcony or the like of an apartment residence to an accumulation place by using an unmanned aerial vehicle. However, the collection object such as garbage may give off an odor that makes people uncomfortable. When collecting garbage placed on the balcony or the like by using the unmanned aerial vehicle, it is necessary to consider the effect on residents when passing near a window or a balcony of the apartment building.

An object of the present disclosure made in view of such circumstances is to provide a control device of an unmanned aerial vehicle, an unmanned aerial vehicle, and a method capable of collecting a collection object such that an odor of the collection object is less likely to be smelt by people there around.

The control device according to an embodiment of the present disclosure includes a control unit configured to control an unmanned aerial vehicle that collects a collection object. The control unit acquires information that indicates an odor intensity of the collection object to be collected, and determines a flight route of the unmanned aerial vehicle after the unmanned aerial vehicle picks up the collection object located at a collection point, based on the information that indicates the odor intensity of the collection object.

The unmanned aerial vehicle according to the embodiment of the present disclosure includes the control unit and is configured to collect the collection object. The control unit acquires information that indicates an odor intensity of the collection object to be collected, and determines a flight route of the unmanned aerial vehicle after the unmanned aerial vehicle picks up the collection object located at a collection point, based on the information that indicates the odor intensity of the collection object.

A method according to one embodiment of the present disclosure is a method executed by a control device that controls an unmanned aerial vehicle that is configured to collect a collection object. The method includes: acquiring information that indicates an odor intensity of the collection object to be collected; and determining a flight route of the unmanned aerial vehicle after the unmanned aerial vehicle picks up the collection object located at a collection point, based on the information that indicates the odor intensity of the collection object.

According to the present disclosure, it is possible to provide a control device of an unmanned aerial vehicle, an unmanned aerial vehicle, and a method capable of collecting a collection object such that an odor of the collection object is less likely to be smelt by people there around.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 5 is a flowchart showing an example of an operation of the control device; and FIG. 6 is a flowchart showing an example of an operation of a control unit of the unmanned aerial vehicle.

DETAILED DESCRIPTION OF EMBODIMENTS

Hereinafter, an embodiment of the present disclosure will be described.

Outline of Embodiment

Figure 1:
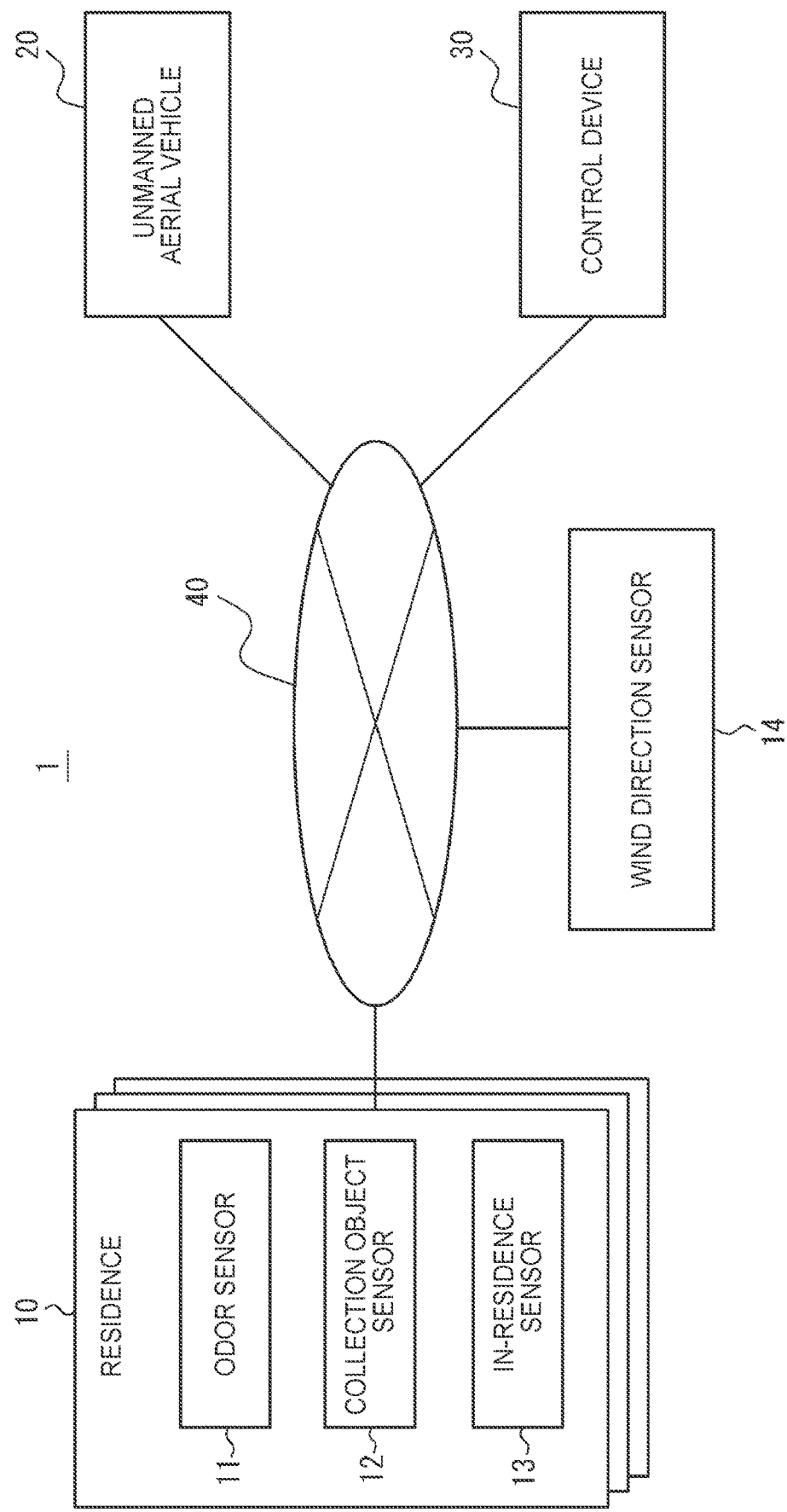
FIG. 1 is a block diagram showing a schematic configuration of a collection object collecting system according to an embodiment of the present disclosure.

The outline of a collection object collecting system 1 according to one embodiment of the present disclosure will be described with reference to FIG. 1. The collection object collecting system 1 includes an odor sensor 11 and a collection object sensor 12 disposed in a plurality of residences 10 of a building such as an apartment residence, an unmanned aerial vehicle 20, and a control device 30. The plurality of residences 10 may further include an in-residence sensor 13. The collection object collecting system 1 may further include a wind direction sensor 14 disposed near the building. The collection object collecting system 1 is a system for collecting a collection object located at a collection point provided on each balcony or the like of the building such as the apartment residence, at an accumulation place using an unmanned aerial vehicle 20. The collection object located at the collection point includes the collection object placed at the collection point, the collection object suspended at the collection point, and the collection object housed in the storage case provided at the collection point.

The odor sensor 11 is disposed near each of the collection points and is configured to measure the odor intensity of the collection object. As the odor sensor 11, a sensor that measures various known odors can be used. The odor sensor 11 includes, for example, a semiconductor type odor sensor, a crystal vibration type odor sensor, an FET biosensor, a film type surface stress sensor, and the like.

The collection object sensor 12 is a sensor that detects whether the collection object is located at the collection point. The collection object sensor 12 can be, for example, a weight sensor disposed under the case for storing the collection object at the collection point.

The in-residence sensor 13 is a sensor other than the odor sensor 11 and the collection object sensor 12, and is provided in each residence 10 of the building such as the apartment residence. Each residence 10 includes the living room and the balcony occupied by each resident. In the present embodiment, in-residence sensor 13 may detect one or more of information that indicates the open-closed state of the window of the residence 10, information that indicates whether there is a person on the balcony of each residence 10, and information that indicates whether there is laundry on the balcony of each residence 10. For example, the in-residence sensor 13 that detects the information that indicates the open-closed state of the window can be a sensor that detects the open-closed state of the window of the residence 10 or a camera capable of capturing the window. However, the in-residence sensor is not limited to the above. Further, for example, as the in-residence sensor 13 that detects information that indicates whether there is a person on the balcony, a camera that captures the balcony with visible light or an infrared camera that detects infrared rays generated from the human body can be used. However, the in-residence sensor 13 is not limited to the above.

The wind direction sensor 14 detects the wind direction around the building that is the target for collecting the collection object. As the wind direction sensor 14, a sensor of any form can be adopted as long as it detects the wind direction. The wind direction sensor 14 may be disposed, for example, on the roof of the building. A plurality of the wind direction sensors 14 may be disposed around the building to detect the wind direction at a plurality of points around the building.

The control device 30 is an information process device such as a computer. The control device 30 can communicate with each of the odor sensor 11 and the collection object sensor 12 in each residence 10, and the unmanned aerial vehicle 20 via a network 40 including, for example, the Internet and a mobile communication network. The control device 30 may further be able to communicate with the in-residence sensor 13 and the wind direction sensor 14 via the network 40. In this embodiment, the unmanned aerial vehicle 20 and the control device 30 may be managed by a business operator that collects the collection object.

The unmanned aerial vehicle 20 is any aerial vehicle that no one is onboard. For example, an aerial vehicle such as a drone and a multicopter can be adopted as the unmanned aerial vehicle 20. The unmanned aerial vehicle 20 is equipped with a camera or the like as described later. The unmanned aerial vehicle 20 can fly autonomously or by cooperating with the control device 30. The unmanned aerial vehicle 20 can move along the flight route acquired from the control device 30. The unmanned aerial vehicle 20 may also be able to autonomously bypass an obstacle when the obstacle is detected by using a camera. The unmanned aerial vehicle 20 can autonomously control its location and attitude according to environmental conditions such as wind or rain.

Figure 2:
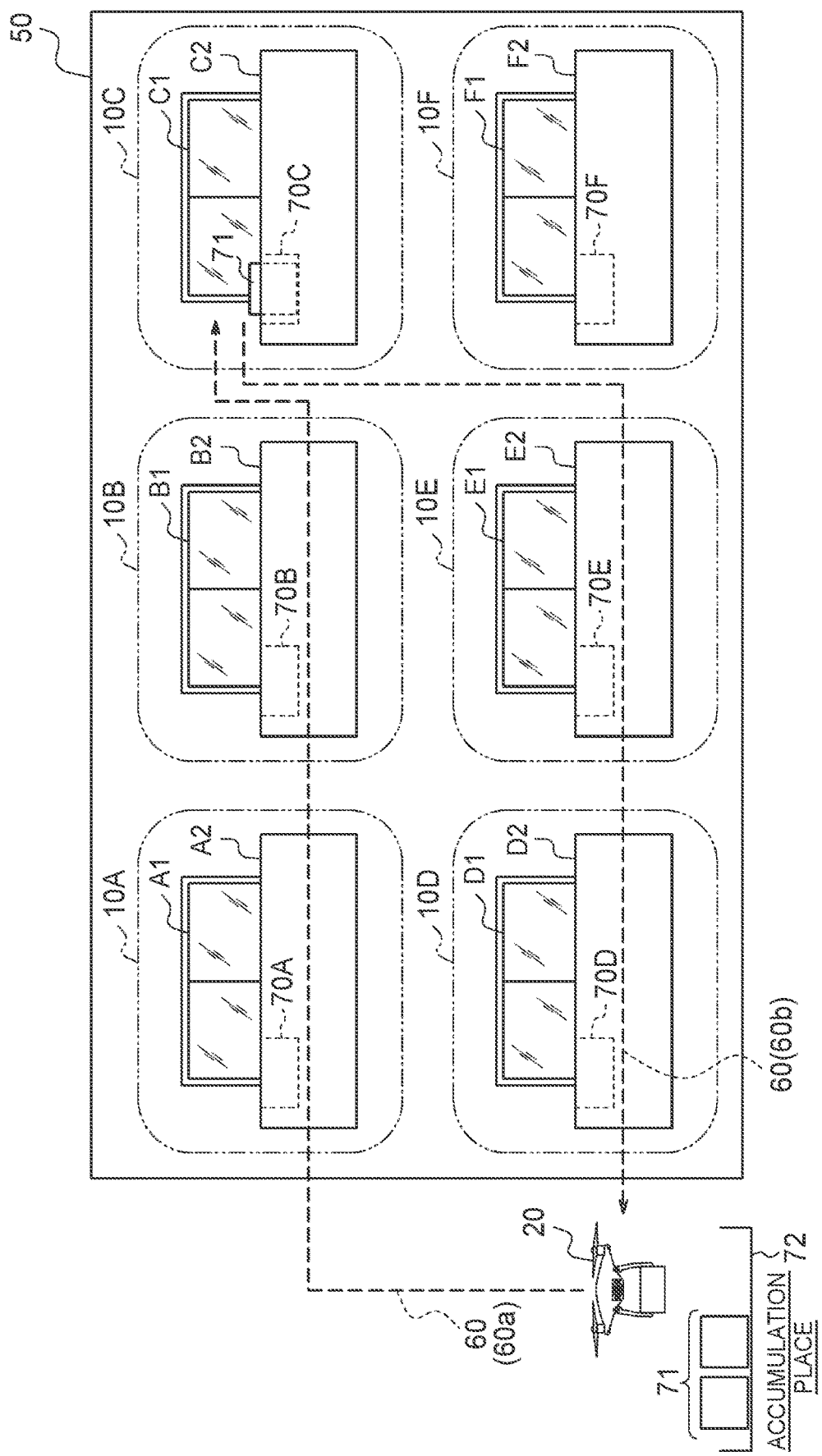
FIG. 2 is a diagram showing an example of a flight route of an unmanned aerial vehicle.

In this embodiment, the unmanned aerial vehicle 20 is used for collecting a collection object such as garbage. The collection object may include odor-generating food waste and the like. For example, as shown in FIG. 2, the unmanned aerial vehicle 20 picks up a collection object 71 located at collection points 70A to 70F on the balcony of each residence 10A to 10F of a building 50 of the apartment residence, and the like, and transports the collection object 71 to an accumulation place 72 of the collection object 71. The accumulation place 72 may be located near the building 50. The collection object 71 may be mounted on a vehicle for transporting the collection object 71 such as a garbage truck or a truck from the accumulation place 72 and transported to a treatment facility of the collection object 71 such as a garbage treatment facility. In the following, the residences 10A to 10F and the collection points 70A to 70F may be appropriately referred to as the "residence 10" and the "collection point 70".

The unmanned aerial vehicle 20 may sequentially collect the collection object 71 from the collection point 70 on the balcony of the building 50 until the collection objects 71 of all the residences 10 are collected at the accumulation place 72. The unmanned aerial vehicle 20 can acquire from the control device 30, information on the collection point 70 at which the collection object 71 is present. For example, as shown in FIG. 2, it is assumed that the collection object 71 remains on a balcony C2 of the residence 10C. The unmanned aerial vehicle 20 moves along the outer wall of the building 50 from the accumulation place 72 to the balcony C2 of the target residence 10C among the plurality of residences 10A to 10F, picks up the collection object 71 at the collection point 70C of the balcony C2, and transports the collection object 71 to the accumulation place 72.

Here, the unmanned aerial vehicle 20 can move along the outer wall surface of the building 50 by keeping a constant distance from the outer wall surface of the building 50, for example. The constant distance is, for example, 1 m, but it is not limited to this. If the distance between the moving unmanned aerial vehicle 20 and the outer wall surface of the building 50 is relatively long, there is a possibility that the inside of the living room of the residences 10A to 10F is unwantedly captured by the camera of the unmanned aerial vehicle 20 through the windows A1 to F1 provided on the outer wall surface. In contrast, when the unmanned aerial vehicle 20 moves along the outer wall of the building 50, the possibility that the inside of the residences 10A to 10F is unwantedly captured by the camera of the unmanned aerial vehicle 20 is reduced and thus, the privacy of the resident is protected.

However, when the unmanned aerial vehicle 20 moves along the outer wall surface of the building 50, the distance between the unmanned aerial vehicle 20 and the outer wall surface of the building 50 is relatively short. Thus, the residents of the building 50 may feel uncomfortable about the odor the collection object 71. Regarding the above, according to the present embodiment, as will be described later, the possibility that the residents of the building 50 feel uncomfortable about the odor of the collection object 71 is reduced.

First, the outline of the present embodiment will be described, and the details will be described later. In the present embodiment, the control device 30 acquires from the collection object sensor 12 of each residence 10 via the network 40, information that indicates whether the collection object 71 is present at collection point 70 of each of the plurality of residences 10 present along the outer wall of the building 50. Further, the control device 30 acquires information that indicates the odor intensity of the collection object 71 from the odor sensor 11 via the network 40. Then, the control device 30 instructs the unmanned aerial vehicle 20 to pick up the collection object 71 at the collection point 70 where the collection object 71 is present. Further, the control device 30 determines a flight route 60b of the unmanned aerial vehicle 20 back to the accumulation place 72, after the unmanned aerial vehicle 20 picks up the collection object 71 located at the collection point 70, based on the information that indicates the odor intensity of the collection object 71. The control device 30 instructs the unmanned aerial vehicle 20 to fly based on the determined flight route 60b. The flight route 60b is a return flight route from the collection point 70 to the accumulation place 72 of an entire flight route 60 of the unmanned aerial vehicle 20.

The control device 30 determines the flight route 60b such that the stronger the odor intensity of the collection object 71, the farther the unmanned aerial vehicle 20 flies while being spaced away from the outer wall of the building 50. By flying while being spaced away from the outer wall of the building 50, the odor of the collection object 71 is more diffused, thus reducing the likelihood that the residents of the residences 10 of the building 50 feel uncomfortable about the odor of the collection object.

Further, when determining the flight route, the control device 30 may take into consideration, detection information by the in-residence sensor 13. The control device 30 can determine the flight route so as to avoid flying in front of the residence 10 that the resident is likely to be affected by the odor. For example, when in-residence sensor 13 detects that the window of the residence 10 is open, or when it detects that there is a person on the balcony of the residence 10, the resident may feel uncomfortable about the odor of the collection object when the unmanned aerial vehicle 20 that carries the collection object passes the front of the residence 10. Further, for example, when there is laundry in the balcony of the residence 10, when the unmanned aerial vehicle 20 carrying the collection object passes in front of the residence 10, the residents may be worried that the odor is transferred to the laundry. Therefore, the control device 30 may determine the flight route so as to not pass in front of the residence 10 or to keep a considerable distance from the residence 10. This improves the technique for controlling the unmanned aerial vehicle 20 in that the possibility that the residents of the building 50 feel uncomfortable about the odor of the collection object 71 carried by the unmanned aerial vehicle 20 is decreased.

For example, in FIG. 2, when there is the collection object 71 at the collection point 70C of the residence 10C, the unmanned aerial vehicle 20 can move to a target residence C along an outbound flight route 60a for collecting the collection object 71. On the outbound route in which the unmanned aerial vehicle 20 goes to collect the collection object 71, the unmanned aerial vehicle 20 may pass in front of any of the residences 10A to 10F. The outbound flight route 60a may be determined by the control device 30 or may be determined autonomously by the unmanned aerial vehicle 20. On the return route to the accumulation place 72 in which the unmanned aerial vehicle 20 picks up the collection object 71 at the collection point 70C, the unmanned aerial vehicle 20 flies in accordance with the flight route 60b determined by the control device 30. For example, when windows A1 and B1 of the residences 10A and 10B are open, or when there are people on balconies A2 and B2, the control device 30 determines the flight route 60b that avoids the front of the residences 10A and 10B and that returns to the accumulation place 72. In the case of FIG. 2, the control device 30 selects the flight route 60b that passes in front of balconies D2 and E2 of the residences 10D and 10E. In such a case, the possibility that the residents in the residences 10A and 10B will feel uncomfortable about the odor of the collection object 71 carried by the unmanned aerial vehicle 20 is reduced.

Next, the configuration of each component of the collection object collecting system 1 will be described in detail.

Configuration of Unmanned Aerial Vehicle

Figure 3:
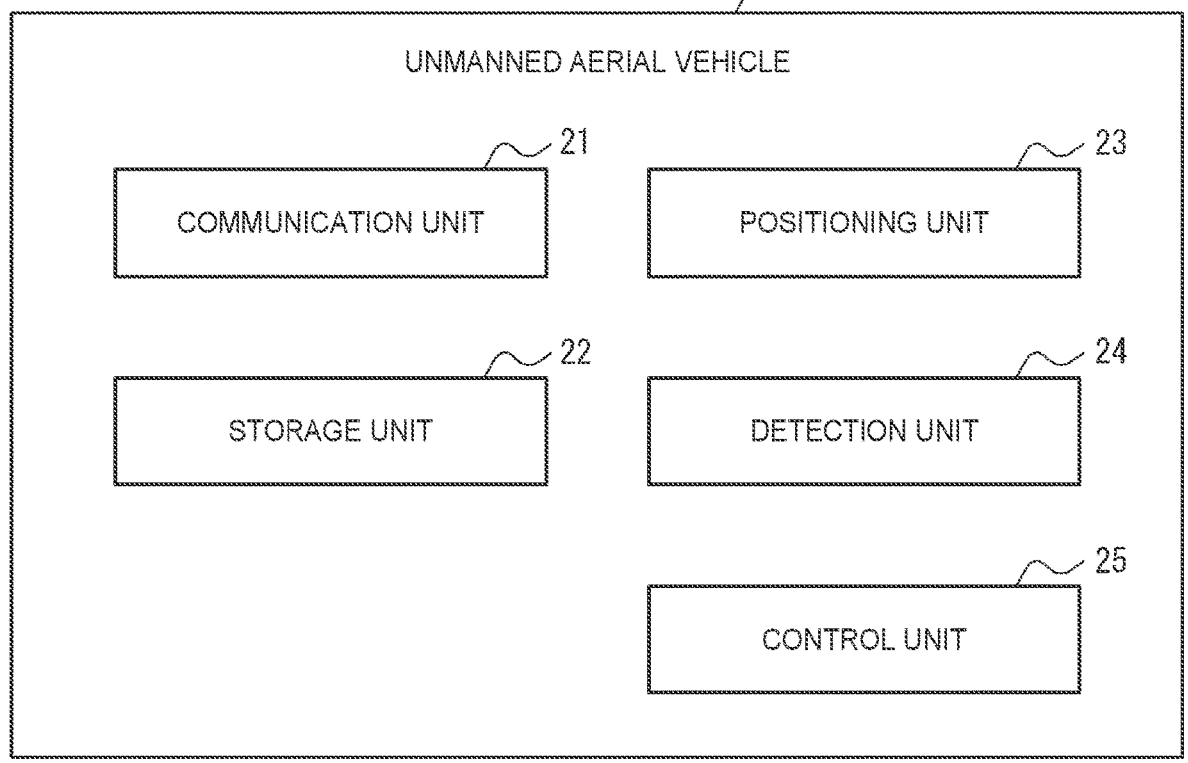
FIG. 3 is a block diagram showing a schematic configuration of the unmanned aerial vehicle.

As shown in FIG. 3, the unmanned aerial vehicle 20 includes a communication unit 21, a storage unit 22, a positioning unit 23, a detection unit 24, and a control unit 25.

The communication unit 21 includes one or more communication interfaces connected to the network 40. The communication interface supports, for example, 4th generation (4G) and 5th generation (5G) mobile communication standards. The supported standards are not limited to these, and the communication interface may support any mobile communication standards. In this embodiment, the unmanned aerial vehicle 20 communicates with the control device 30 via the communication unit 21. The communication unit 21 can receive from the control device 30, information on the flight route of the unmanned aerial vehicle 20 after picking up the collection object.

The storage unit 22 includes one or more memories. The memories are, for example, a semiconductor memory, a magnetic memory, or an optical memory, but are not limited to these memories. Each memory included in the storage unit 22 may function as, for example, a main storage device, an auxiliary storage device, or a cache memory. The storage unit 22 stores any information used for the operation of the unmanned aerial vehicle 20. For example, the storage unit 22 may store a system program, an application program, and embedded software. The information stored in the storage unit 22 may be updatable with information received from the network 40 via the communication unit 21, for example. The storage unit 22 may store the information on the location of the collection point 70 of each residence 10 and the information on the flight route 60 received from the control device 30.

The positioning unit 23 includes a receiver compatible with a satellite positioning system. The receiver is compatible with, for example, the Global Positioning System (GPS), but the compatible satellite positioning system is not limited to this, and the receiver may be compatible with any satellite positioning system. The positioning unit 23 also includes, for example, a gyro sensor, a geomagnetic sensor, and a barometric pressure sensor. In the present embodiment, the unmanned aerial vehicle 20 can acquire the location information of the own machine, the direction in which the unmanned aerial vehicle 20 is facing, and the inclination of the own machine by using the positioning unit 23. The location information may include two-dimensional coordinate data including latitude and longitude, and may include three-dimensional coordinate data including altitude in addition to latitude and longitude.

The detection unit 24 includes one or more sensors used for detecting obstacles existing around the unmanned aerial vehicle 20. In the present embodiment, the sensor includes, but is not limited to, a camera. The one or more sensors may further include, for example, millimeter wave radar or light detection and ranging (LiDAR). The output information of the sensors of the detection unit 24 can be used, for example, for the unmanned aerial vehicle 20 to fly while autonomously bypassing obstacles around the unmanned aerial vehicle 20.

The detection unit 24 may include other types of sensors that acquire information around the unmanned aerial vehicle 20. In one embodiment, the detection unit 24 may include a sensor that detects the odor of the collection object 71 in place of the odor sensor 11 or in addition to the odor sensor 11 disposed in the residence 10. As a result, the unmanned aerial vehicle 20 may detect the odor intensity of the collection object picked up at the collection point 70.

The control unit 25 includes one or more processors, one or more programmable circuits, one or more dedicated circuits, or a combination of these. The processors are, for example, a general-purpose processor such as a central process unit (CPU) or a graphics process unit (GPU), or a dedicated processor specialized for a specific process, but are not limited to these processors. The programmable circuits are, for example, a field-programmable gate array (FPGA), but are not limited to the circuit. The dedicated circuits are, for example, an application specific integrated circuit (ASIC), but are not limited to the circuit. The control unit 25 controls the operation of the entire unmanned aerial vehicle 20. The control unit 25 can move the unmanned aerial vehicle 20 following the flight route 60 stored in the storage unit 22 by using the location information and the like acquired by the positioning unit 23.

Configuration of Control Device

Figure 4:
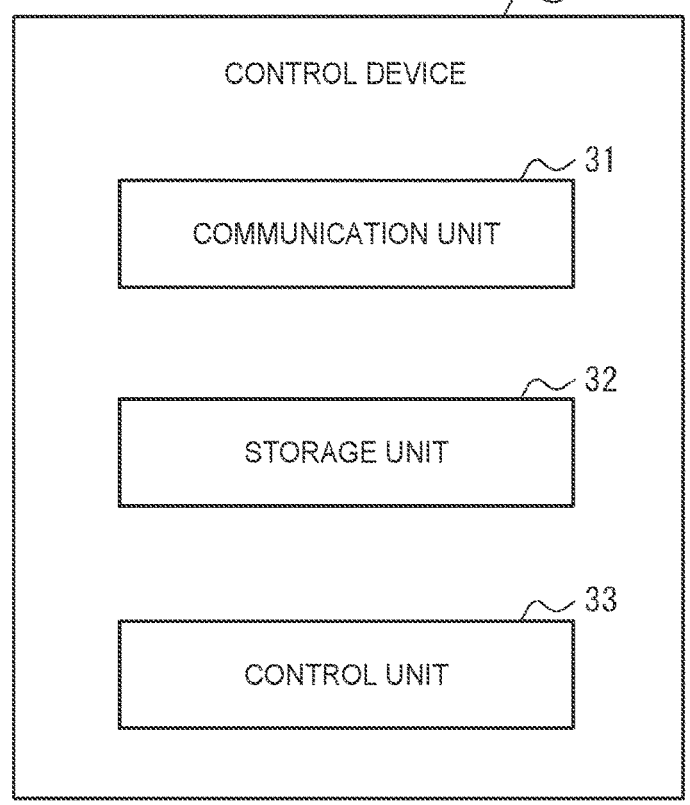
FIG. 4 is a block diagram showing a schematic configuration of a control device.

As shown in FIG. 4, the control device 30 includes a communication unit 31, a storage unit 32, and a control unit 33.

The communication unit 31 includes one or more communication interfaces connected to the network 40. The communication interfaces support, for example, a mobile communication standard, a wired local area network (LAN) standard, or a wireless LAN standard, but the supported standards are not limited to these, and the communication interfaces may support any communication standard. In the present embodiment, the control device 30 communicates with the odor sensor 11, the collection object sensor 12, the in-residence sensor 13, and the unmanned aerial vehicle 20 in each residence 10 via the communication unit 31.

The storage unit 32 includes one or more memories. Each memory included in the storage unit 32 may function as, for example, a main storage device, an auxiliary storage device, or a cache memory. The storage unit 32 stores any information used for the operation of the control device 30. For example, the storage unit 32 may store a system program, an application program, a database, and map information. The information stored in the storage unit 32 may be updatable with information received from the network 40 via the communication unit 31, for example.

In this embodiment, the storage unit 32 stores information about one or more buildings 50 in which the collection object 71 is collected. The information of the building 50 includes any information used to determine the flight route 60 for the unmanned aerial vehicle 20 to travel along the outer wall of the building 50 to the target residence 10 so as to collect the collection object 71. For example, the information about the building 50 includes, but is not limited to, three-dimensional survey data of the building 50 and three-dimensional coordinate data indicating the location of the accumulation place 72 of the collection object 71 associated with the building 50.

The three-dimensional survey data of the building 50 is, for example, a plurality of three-dimensional coordinate data (that is, three-dimensional point cloud data) corresponding to the building 50. information that indicates which of the outer wall of the building 50, the window of each residence 10, and the balcony of each residence 10 each of the three-dimensional coordinate data corresponds to is associated with each of the plurality of three-dimensional coordinate data, for example. Based on the three-dimensional survey data of the building 50, the control device 30 is able to identify each of the outer wall of the building 50, the location of each residence 10, the location of the window of each residence 10, the location of the balcony of each residence 10, and the location of the collection point 70 provided inside of the balcony.

The control unit 33 includes one or more processors, one or more programmable circuits, one or more dedicated circuits, or a combination of these. The control unit 33 controls the operation of the entire control device 30. Details of the operation of the control device 30 controlled by the control unit 33 will be described later.

Operation Flow of Control Device

An example of the operation of the control device 30 according to the present embodiment will be described with reference to FIG. 5. In the example of FIG. 5, it is assumed that the odor sensor 11, the collection object sensor 12, and the in-residence sensor 13 are all present in the residence 10.

Step S101: The control unit 33 of the control device 30 acquires, from the storage unit 32, information on the building 50 in which the collection object 71 is collected and information on the accumulation place 72 associated with the building 50.

Step S102: The control unit 33 recognizes the residence 10 having the collection object 71 at the collection point 70, based on the information from the collection object sensor 12 of each residence 10. In the following steps S103 to S108, a process of sequentially collecting the collection object 71 of each residence 10 recognized in step S102 is executed.

Step S103: The control unit 33 acquires information that indicates the odor intensity of the collection object 71 from the odor sensor 11 of the residence 10 recognized that the collection object 71 is present. The control unit 33 may count the number of times a case in which the odor intensity of the collection object is stronger than a predetermined threshold value occurs, for the collection point 70 of each residence 10, and the control unit 33 may store the number in the storage unit 32. The information on the number of occurrences stored in the storage unit 32 can be used for alerting the resident of each residence 10 to reduce collection objects having a strong odor, or for charging an additional fee for collecting the collection object having a strong odor.

Step S104: The control unit 33 acquires the detection information detected in each residence 10 from the in-residence sensor 13 of each residence 10. As described above, the detection information may include one or more of the information that indicates the open-closed state of the window of the residence 10, the information that indicates whether there is a person on the balcony of each residence 10, and the information that indicates whether there is laundry on the balcony of each residence 10. Step S104 is not essential.

Step S105: The control unit 33 acquires the wind direction information from the wind direction sensor 14 provided in the building 50. Step S105 is not essential.

The order of steps S103 to S105 is interchangeable with each other. Steps S103 to S105 may be executed in parallel.

Step S106: The control unit 33 determines the flight route 60b on the return route toward the accumulation place 72 after the unmanned aerial vehicle 20 has picked up the collection object 71. The flight route 60b is determined using the three-dimensional survey data of the building 50. The method of determining the flight route 60b will be described below.

The control unit 33 may determine the distance from the building 50 in accordance with the odor intensity of the collection object 71 acquired in step S103. For example, the control unit 33 may provide flying instructions such that the unmanned aerial vehicle 20 flies at a location 1m away from the outer wall of the building 50 when the intensity of the quantified odor is smaller than a first predetermined value. For example, the control unit 33 may provide flying instructions such that the unmanned aerial vehicle 20 flies at a location 3m away from the outer wall of the building 50 when the intensity of the quantified odor is larger than a second predetermined value. Here, the distances of 1 m and 3 m are examples. The control unit 33 may set the distance from the outer wall of the building 50 to an arbitrary value in accordance with the odor intensity of the collection object 71.

Based on the detection information detected by the in-residence sensor 13 of each residence 10 acquired in step S104, the control unit 33 may determine whether to pass in front of the balcony of any of the residences 10 and whether to not pass in front of the balcony of any of the residences 10. For example, the control unit 33 may score the degree to which the unmanned aerial vehicle 20 should not pass in front of each residence 10 and may determine the flight route 60*b* to pass in front of the residence with a low score. For example, when the window is open, when there is a person on the balcony, and when there is laundry on the balcony, the control unit 33 may add a score to each corresponding residence 10 and may decrease the possibility of selecting the flight route 60*b* passing in front of the above residence 10.

The control unit 33 may consider the wind direction information acquired in step S105 when determining the distance between the outer wall of the building 50 and the flight route 60*b* of the unmanned aerial vehicle 20. When the unmanned aerial vehicle 20 is located upwind of the outer wall of the building 50, the control unit 33 may determine the flight route 60*b* such that the unmanned aerial vehicle 20 flies while being spaced away from the outer wall, when the unmanned aerial vehicle 20 is located downwind of the outer wall. For example, when the unmanned aerial vehicle 20 is located on the upwind of the outer wall, the control unit 33 may set the distance between the flight route 60*b* of the unmanned aerial vehicle 20 and the outer wall to be twice as much as the distance when there is no wind. Here, the distance being multiplied by two is an example. The control unit 33 can set an arbitrary scale. For example, when the unmanned aerial vehicle 20 is located downwind of the outer wall, the control unit 33 may set the distance between the flight route 60*b* of the unmanned aerial vehicle 20 and the outer wall to a relatively short distance, such as 1 m, regardless of the odor intensity of the collection object 71.

Step S107: The control unit 33 transmits the return flight route 60*b* determined in step S106 after the collection object 71 is picked up to the unmanned aerial vehicle 20 via the communication unit 31 and instructs the unmanned aerial vehicle 20 to collect the collection object 71. The control unit 33 may determine and transmit the outbound flight route 60*a* toward the collection point 70 of the collection object 71 to the unmanned aerial vehicle 20 by any method. The control unit 33 may transmit only the location information of the collection point 70 to the unmanned aerial vehicle 20 regarding the outbound route, and the unmanned aerial vehicle 20 may autonomously determine the outbound flight route 60*a* toward the collection point 70. After picking up the collection at the collection point 70, the unmanned aerial vehicle 20 transports the collection object 71 to the accumulation place 72 in accordance with the return flight route 60*b* received from the control device 30.

The control unit 33 may cause the unmanned aerial vehicle 20 to start the outbound flight toward the collection point 70 at any time between steps S102 and S106, instead of after step S106. In this case, when the unmanned aerial vehicle 20 picks up the collection object 71 at the collection point 70, the control unit 33 determines the return flight route 60*b* based on the latest odor intensity of the odor sensor 11, the detection information of the in-residence sensor 13, and the wind direction information of the wind direction sensor 14.

Step S108: When the unmanned aerial vehicle 20 completes the transportation of the collection object 71 to the accumulation place 72, the control unit 33 determines the process of collecting the next collection object 71 when there is the remaining collection object 71 to be collected in any of the residences 10 (step S108: NO). In this case, the control unit 33 returns to step S103 and repeats the processes of steps S103 to S107 for the next collection object 71. When all the collection objects 71 have been collected (step S108: YES), the control unit 33 ends the process.

As described above, the control device 30 according to the present embodiment determines the flight route 60*b* of the unmanned aerial vehicle 20 that collects the collection object 71 located at the collection point 70 of each of the plurality of residences 10 present along the outer wall of the building 50. The control device 30 determines the flight route 60*b* of the unmanned aerial vehicle 20 based on the information that indicates the odor intensity. With such a configuration, the control device 30 can make the unmanned aerial vehicle 20 fly such that the residents of the building 50 do not feel uncomfortable about the odor of the collection object 71.

Further, the control device 30 according to the present embodiment can determine the flight route 60*b* of the unmanned aerial vehicle 20 in consideration of at least one or more information such as the open-closed state of the window of the residence 10, the presence or absence of a person on the balcony, the presence or absence of laundry, and the wind direction. This makes it possible to further reduce the possibility that the residents of the building 50 will feel uncomfortable about the odor of the collection object 71.

In the above embodiment, the odor sensor 11, the collection object sensor 12, and the in-residence sensor 13 are provided in each residence 10. However, the unmanned aerial vehicle 20 can acquire the information that indicates the odor intensity, the information that indicates the presence or absence of collection objects, the window opening-closing information, the information on whether there is a person on the balcony, and the information on whether there is laundry. For example, the unmanned aerial vehicle 20 may have a sensor that measures the odor of the collection object that is picked up. Further, the unmanned aerial vehicle 20 may determine whether there is the collection object 71 in each residence 10 by capturing an image of the collection point 70 with the camera and performing image process with the control unit 25. The unmanned aerial vehicle 20 may capture the balcony of each residence 10 and determine the open-closed state of the window, the presence or absence of a person on the balcony, and the presence or absence of laundry by image processing. Further, the unmanned aerial vehicle 20 may acquire the image and transmit the acquired image to the control device 30. In this case, the image process is performed by the control unit 33 of the control device 30.

The wind direction sensor 14 does not have to be disposed in the building 50. For example, the unmanned aerial vehicle 20 performs a control to maintain the own machine at a predetermined location, when there is wind. For example, the unmanned aerial vehicle 20 needs to generate propulsive force in the windward direction in order to maintain the location of the own machine when there is wind. Thus, the control unit 25 of the unmanned aerial vehicle 20 can detect the wind direction from the control information of the own machine. Therefore, the control device 30 can acquire the wind direction information from the unmanned aerial vehicle 20.

(When Unmanned Aerial Vehicle Determines Flight Route)

The return flight route 60b of the unmanned aerial vehicle 20 may be determined by the control unit 25 of the unmanned aerial vehicle 20 instead of the control unit 33 of the control device 30. All or part of the process performed by the control unit 33 of the control device 30 described in the above embodiment may be executed by the control unit 25 of the unmanned aerial vehicle 20.

(Process Flow of Control Unit of Unmanned Aerial Vehicle)

With reference to FIG. 6, described is an example of the process flow of the control unit 25 when the control unit 25 of the unmanned aerial vehicle 20 determines the flight route 60. In the example of FIG. 6, it is assumed that each residence 10 does not have the odor sensor 11 and the collection object sensor 12 described in FIG. 1, and the building 50 does not have the wind direction sensor 14. The information of the in-residence sensor 13 is provided to the unmanned aerial vehicle 20 directly or indirectly via the control device 30. Further, it is assumed that the detection unit 24 of the unmanned aerial vehicle 20 includes an odor sensor that detects the odor intensity of the collected collection object 71 that is picked up. It is assumed that the control device 30 provides the unmanned aerial vehicle 20 with the information regarding the building 50 and the accumulation place 72.

Step S201: The control unit 25 of the unmanned aerial vehicle 20 acquires from the control device 30, the information on the building 50 in which the collection object 71 is collected and the information on the accumulation place 72 associated with the building 50, in which the above information are stored in the storage unit 32.

Step S202: The control unit 25 starts the search for the collection object 71 in accordance with the instruction of the operator of the unmanned aerial vehicle 20 or the like. The unmanned aerial vehicle 20 may sequentially pass in front of the residence 10 and search for the collection object 71 at the collection point 70. The unmanned aerial vehicle 20 may analyze the image acquired by the camera of the detection unit 24 to determine the presence or absence of the collection object 71. As another method, the unmanned aerial vehicle 20 may first capture the balcony of each residence 10 with the camera to acquire information on all collection points 70 where the collection object 71 is located.

Step S203: When the control unit 25 discovers the collection object 71, the control unit 25 performs an operation of picking up the collection object 71.

Step S204: The control unit 25 causes the odor sensor of the detection unit 24 to detect the odor intensity of the collection object 71, and acquires information that indicates the odor intensity.

Step S205: The control unit 25 acquires the detection information detected in each residence 10 from the in-residence sensor 13 of each residence 10. As described above, the detection information may include the information that indicates the open-closed state of the window of the residence, the information that indicates whether there is a person on the balcony of each residence 10, and the information that indicates whether there is laundry on the balcony of each residence 10. Step S205 is not essential.

Step S206: The control unit 25 recognizes the wind direction from the control information that controls the location and attitude of the own machine (unmanned aerial vehicle 20). Step S206 is not essential.

Step S207: The control unit 25 determines the return flight route 60b toward the accumulation place 72 after the collection object 71 is picked up. The method for determining the flight route 60b is the same as in step S106.

Step S208: The control unit 25 controls the unmanned aerial vehicle 20 so as to carry the collection object 71 to the accumulation place 72 following the flight route 60b determined in step S207.

Step S209: The control unit 25 repeats the processes of steps S203 to S208 when there is the collection object 71 that the unmanned aerial vehicle 20 has not yet collected (step S209: NO). When the unmanned aerial vehicle 20 confirms the collection points 70 of all the residences 10 and the collection of all collection objects 71 is completed (step S209: YES), the control unit 25 ends the process.

Even when the control unit 25 of the unmanned aerial vehicle 20 determines the flight route 60b, the unmanned aerial vehicle 20 can be flown such that the residents of the building 50 are unlikely to feel uncomfortable about the odor of the collection object 71, as in the case where the control unit 33 of the control device 30 determines the flight route 60b.

Although the present disclosure has been described above based on the drawings and the embodiment, it should be noted that those skilled in the art may make various modifications and alterations thereto based on the present disclosure. It should be noted, therefore, that these modifications and alterations are within the scope of the present disclosure. For example, the functions included in the configurations, steps, etc. can be rearranged so as not to be logically inconsistent, and a plurality of configurations, steps, etc. can be combined into one or divided.

For example, in the above embodiment, the configuration and operation of the control device 30 may be distributed to a plurality of information processing devices capable of communicating with each other. Further, in the above-described embodiment, the case where the number of residences 10 present along the outer wall of the building 50 is two or more has been described. However, the number of residences may be one. Further, the place at which the unmanned aerial vehicle 20 collects the collection object 71 is not limited to inside the residence in one building 50. The unmanned aerial vehicle 20 may collect the collection object 71 from a plurality of nearby buildings.

An embodiment is also possible in which, for example, a general-purpose drone or a computer functions as the unmanned aerial vehicle 20 or the control device 30 in accordance with the above-described embodiment. Specifically, a program describing process contents for realizing each function of the unmanned aerial vehicle 20 or the control device 30 according to the above-described embodiment is stored in the memory of a general-purpose drone or a computer, and the program is read out and executed by the processor. Therefore, the disclosure according to the present embodiment can also be realized as a program that can be executed by a processor or a non-transitory computer-readable medium that stores the program.

What is claimed is:
1. A control device comprising a control unit configured to control an unmanned aerial vehicle that collects a collection object, wherein the control unit is configured to:
  acquire information that indicates an odor intensity of the collection object to be collected, and
  determine a flight route of the unmanned aerial vehicle after the unmanned aerial vehicle picks up the collection object located at a collection point, based on the information that indicates the odor intensity of the collection object,
the unmanned aerial vehicle is configured to collect the collection object from the collection point that is present along an outer wall of a building, and
the control unit is configured to determine the flight route to be provided along the outer wall of the building.

2. The control device according to claim 1, wherein the control unit is configured to determine the flight route such that the stronger the odor intensity, the farther the unmanned aerial vehicle flies while being spaced away from the outer wall.

3. The control device according to claim 1, wherein
there is a plurality of residences present along the outer wall of the building, and
the collection point is located on a balcony disposed along an outer wall of each residence of the plurality of residences.

4. The control device according to claim 3, wherein the control unit is configured to:
acquire detection information from an in-residence sensor disposed in each residence of the plurality of residences, and
determine the flight route in consideration of the detection information.

5. The control device according to claim 4, wherein
the detection information includes opening-closing information of a window along the outer wall of each residence of the plurality of residences, and
the control unit is configured to determine the flight route so as not to fly in front of a residence having an open window.

6. The control device according to claim 5, wherein
the detection information includes information on whether there is a person on the balcony of each residence of the plurality of residences, and
the control unit is configured to determine the flight route so as not to fly in front of the balcony in which the person is present.

7. The control device according to claim 5, wherein
the detection information includes information on whether there is laundry on the balcony of each residence of the plurality of residences, and
the control unit is configured to determine the flight route so as not to fly in front of the balcony in which the laundry is present.

8. The control device according to claim 1, wherein
the control unit is configured to acquire wind direction information, and
in a case where the unmanned aerial vehicle is located upwind of the outer wall, the control unit is configured to determine the flight route such that the unmanned aerial vehicle flies while being spaced away from the outer wall as compared with a case where the unmanned aerial vehicle is located downwind of the outer wall.

9. The control device according to claim 8, wherein the control unit is configured to acquire the wind direction information from the unmanned aerial vehicle.

10. The control device according to claim 1, wherein the control unit is configured to acquire information that indicates the odor intensity of the collection object detected by an odor sensor located at the collection point.

11. The control device according to claim 1, wherein the control unit is configured to count the number of times a case in which the odor intensity of the collection object is stronger than a predetermined threshold value occurs, for each collection point of a plurality of the collection points.

12. An unmanned aerial vehicle that is provided with a control unit and that is configured to collect a collection object, wherein
the control unit is configured to:
  acquire information that indicates an odor intensity of the collection object to be collected,
  determine a flight route of the unmanned aerial vehicle after the unmanned aerial vehicle picks up the collection object located at a collection point, based on the information that indicates the odor intensity of the collection object,
the unmanned aerial vehicle is configured to collect the collection object from the collection point that is present along an outer wall of a building, and
the control unit is configured to determine the flight route to be provided along the outer wall of the building.

13. The unmanned aerial vehicle according to claim 12, wherein the control unit is configured to determine the flight route such that the stronger the odor intensity, the farther the unmanned aerial vehicle flies while being spaced away from the outer wall.

14. The unmanned aerial vehicle according to claim 12, wherein
there is a plurality of residences present along the outer wall of the building, and
the collection point is located on a balcony disposed along an outer wall of each residence of the plurality of residences.

15. A method executed by a control device that controls an unmanned aerial vehicle that is configured to collect a collection object, the method comprising:
acquiring information that indicates an odor intensity of the collection object to be collected; and
determining a flight route of the unmanned aerial vehicle after the unmanned aerial vehicle picks up the collection object located at a collection point, based on the information that indicates the odor intensity of the collection object, wherein
the unmanned aerial vehicle is configured to collect the collection object from the collection point that is present along an outer wall of a building, and
the method includes determining the flight route to be provided along the outer wall of the building.

16. The method according to claim 15, wherein the flight route is determined such that the stronger the odor intensity, the farther the unmanned aerial vehicle flies while being spaced away from the outer wall.

17. The method according to claim 15, wherein
there is a plurality of residences present along the outer wall of the building, and
the collection point is located on a balcony disposed along an outer wall of each residence of the plurality of residences.

* * * * *